(12) United States Patent
Bedard et al.

(10) Patent No.: US 7,597,017 B2
(45) Date of Patent: Oct. 6, 2009

(54) HUMAN LOCOMOTION SIMULATOR

(75) Inventors: Stephane Bedard, Saint-Augustin-de-Desmaures (CA); Pierre Fecteau, Saint-Augustin-de-Desmaures (CA); Pierre-Olivier Roy, Quebec (CA)

(73) Assignee: Victhom Human Bionics, Inc., St-Augustin-de-Desmaures (Québec) (CA)

( * ) Notice: Subject to any disclaimer, the term of this patent is extended or adjusted under 35 U.S.C. 154(b) by 85 days.

(21) Appl. No.: 11/880,164

(22) Filed: Jul. 20, 2007

(65) Prior Publication Data

US 2008/0021570 A1 Jan. 24, 2008

Related U.S. Application Data

(60) Provisional application No. 60/832,138, filed on Jul. 21, 2006.

(51) Int. Cl.
*G09B 19/10* (2006.01)
(52) U.S. Cl. ............... 73/866.4; 73/865.3; 73/865.4; 623/38; 623/47; 623/53; 434/256
(58) Field of Classification Search ............ 73/865.3, 73/865.4, 866.4; 434/256; 623/27–56
See application file for complete search history.

(56) References Cited

U.S. PATENT DOCUMENTS

| | | | | |
|---|---|---|---|---|
| 2,638,776 A | * | 5/1953 | Aines | 73/7 |
| 4,096,733 A | * | 6/1978 | Cohen | 73/7 |
| 4,349,339 A | * | 9/1982 | Daniel | 434/274 |
| 4,432,223 A | * | 2/1984 | Paquette et al. | 73/7 |
| 4,569,352 A | * | 2/1986 | Petrofsky et al. | 607/49 |
| 4,850,877 A | * | 7/1989 | Mason et al. | 434/274 |
| 5,014,719 A | * | 5/1991 | McLeod | 600/587 |
| 5,295,929 A | * | 3/1994 | Weisz | 782/54 |
| 5,344,316 A | | 9/1994 | Hordijk et al. | |
| 5,476,441 A | * | 12/1995 | Durfee et al. | 602/23 |
| 5,695,432 A | * | 12/1997 | Soderlund | 482/69 |
| 5,741,989 A | * | 4/1998 | Viano et al. | 73/866.4 |
| 6,120,290 A | | 9/2000 | Fukushima et al. | |

(Continued)

FOREIGN PATENT DOCUMENTS

DE 2728007 B1 * 8/1978

(Continued)

*Primary Examiner*—David A. Rogers
(74) *Attorney, Agent, or Firm*—Polsinelli Shughart PC; Timothy J. Keefer

(57) ABSTRACT

The present invention discloses locomotion simulator comprising a base having a surface movable along a base axis, a post mounted to the base a pelvic structure and a hip-thigh mechanism wherein coordinated displacement of the pelvic structure and pivoting of the thigh segment assembly simulates patterns of locomotion. The pelvic structure includes a first support movably mounted to the post, the first support allowing a displacement of the pelvic structure along a first pelvic axis generally perpendicular to the base axis and a second support movably mounted to the first support, the second support allowing a displacement of the pelvic structure along a second pelvic axis generally parallel to the base axis. As for the hip-thigh mechanism, it is mounted to the second support and includes a hip joint having a pivot axis generally perpendicular to the displacement of the second support and a thigh segment assembly pivotally so connected to the hip joint as to pivot in a plan defined by the first and second pelvic axes.

36 Claims, 8 Drawing Sheets

U.S. PATENT DOCUMENTS

| | | | |
|---|---|---|---|
| 6,532,400 B1 * | 3/2003 | Jacobs | 700/245 |
| 6,755,870 B1 * | 6/2004 | Biedermann et al. | 623/24 |
| 6,821,233 B1 * | 11/2004 | Colombo et al. | 482/54 |
| 6,912,900 B1 * | 7/2005 | Park et al. | 73/379.01 |
| 7,041,069 B2 * | 5/2006 | West | 601/5 |
| 7,125,388 B1 * | 10/2006 | Reinkensmeyer et al. | 601/5 |
| 7,164,967 B2 * | 1/2007 | Etienne-Cummings et al. | 700/245 |
| 7,279,009 B2 * | 10/2007 | Herr et al. | 623/44 |
| 7,415,903 B2 * | 8/2008 | Crossman et al. | 73/866.4 |
| 2004/0143198 A1 * | 7/2004 | West | 601/5 |
| 2004/0254771 A1 * | 12/2004 | Riener et al. | 703/7 |
| 2008/0109081 A1 * | 5/2008 | Bao et al. | 623/17.15 |
| 2008/0114272 A1 * | 5/2008 | Herr et al. | 600/595 |
| 2008/0255488 A1 * | 10/2008 | Agrawal et al. | 602/23 |

FOREIGN PATENT DOCUMENTS

| | | | |
|---|---|---|---|
| DE | 10060466 A1 | * | 6/2002 |
| FR | 2203279 A | * | 6/1974 |
| JP | 58165032 A | * | 9/1983 |
| JP | 02047530 A | * | 2/1990 |
| JP | 2001191272 A | * | 7/2001 |
| JP | 2005262374 A | * | 9/2005 |
| SU | 1477402 A1 | * | 5/1989 |
| SU | 1509067 A1 | * | 9/1989 |
| WO | WO 03/001483 A1 | | 1/2003 |

* cited by examiner

HUMAN LOCOMOTION SIMULATOR

CROSS-REFERENCE TO RELATED APPLICATION

The present application claims the benefits of U.S. provisional patent application No. 60/832,138 filed Jul. 21, 2006, which is hereby incorporated by reference.

TECHNICAL FIELD

The present invention relates to simulators. More specifically, the present invention is concerned with a human locomotion simulator.

BACKGROUND

Over the years, many kinds of leg prostheses have been devised in effort to replace the leg or legs that amputees have lost. All these leg prostheses have the difficult task of giving to these amputees a gait as normal as possible. The complexity of human locomotion, however, is such that conventional leg prostheses have until now only been using passive mechanisms where the "computerized" passive leg prosthesis are considered on the market as the most sophisticated available devices. Conventional leg prostheses are very limited compared to a real human leg and some needs were thus not entirely fulfilled by them.

According to amputees, specific conditions of use of conventional leg prostheses, such as repetitive movements, continuous loading and assisted mobility from the amputee, typically entail problems such as increases in metabolic energy expenditures, increases of socket pressure, limitations of locomotion speeds, discrepancies in the locomotion movements, disruptions of postural balance, disruptions of the pelvis-spinal column alignment, and increases in the use of postural clinical rehabilitation programs.

Another problem is that during the amputees' locomotion, energy used for moving the prosthesis mainly originates from the amputees themselves because conventional leg prostheses do not have self-propulsion capabilities. This has considerable short and long-term negative side effects. Recent developments in the field of energy-saving prosthetic components have partially contributed to improve the energy transfer between the amputees and their prosthesis. Nevertheless, the problem of energy expenditure is still not fully resolved and remains a major concern in the field of prosthesis and orthosis.

The difficulty related to the development of such complex leg prostheses design is compounded by the lack of testing equipment that realistically simulate human locomotion. The use of such testing equipment would allow the designers to perfect the leg prosthesis at early design stages. As well, a human locomotion simulator would permit, throughout the development, to test efficiently in controlled conditions the performance of prosthesis in various conditions such as walking, running, ascending or descending stairs, for example. Moreover, the use of such simulator means that the whole development and the perfecting of leg prosthesis is carried out without clinical trials with humans; which is benefic in terms of security. Furthermore, without limiting to this specific application, such testing equipment could be used also to test footwear to simulate more realistic environment of use.

Considering this background, it clearly appears that there was a need to develop a human locomotion simulator for the simulation of various types of gaits.

SUMMARY

In accordance with an illustrative embodiment of the present invention, there is provided a locomotion simulator comprising:
  a base having a surface movable along a base axis;
  a post mounted to the base;
  a pelvic structure including:
    a first support movably mounted to the post, the first support allowing a displacement of the pelvic structure along a first pelvic axis generally perpendicular to the base axis;
    a second support movably mounted to the first support, the second support allowing a displacement of the pelvic structure along a second pelvic axis generally parallel to the base axis;
  a hip-thigh mechanism mounted to the second support, the hip-thigh mechanism including:
    a hip joint having a pivot axis generally perpendicular to the displacement of the second support;
    a thigh segment assembly pivotally so connected to the hip joint as to pivot in a plan defined by the first and second pelvic axes;
  wherein coordinated displacement of the pelvic structure and pivoting of the thigh segment assembly simulates patterns of locomotion.

BRIEF DESCRIPTION OF THE FIGURES

Embodiments of the invention will be described by way of example only with reference to the accompanying drawings, in which.

DETAILED DESCRIPTION

Figure 1:
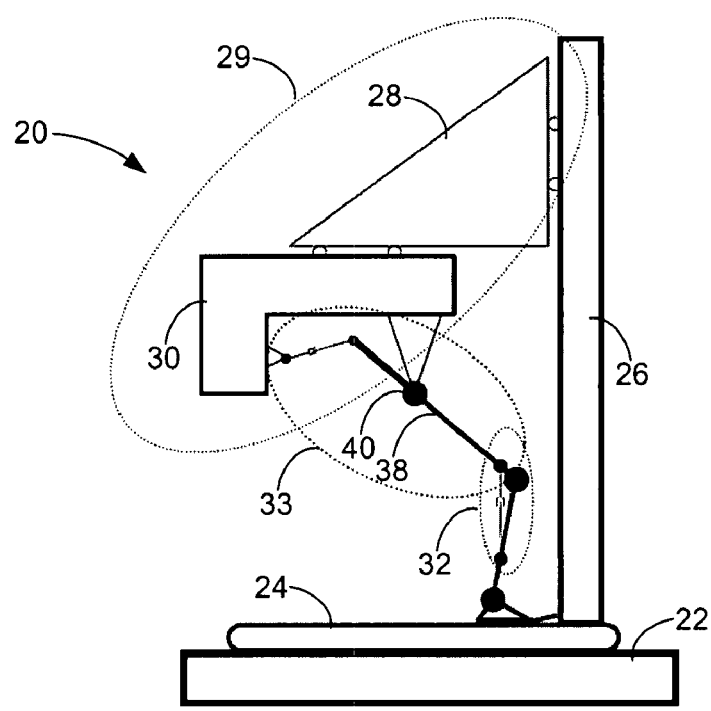
FIG. 1 is a schematic side elevational representation of the mechanical components of a human locomotion simulator according to an illustrative embodiment of the present invention, the stimulator being illustrated with a prosthesis leg attached.

Generally stated the present invention is concerned with the simulation of human locomotion. FIG. 1 schematically illustrates the mechanical components of a human locomotion simulator 20 according to an illustrative embodiment of the present invention. The human locomotion simulator 20 is mainly concerned with locomotion patterns of the human body by the fully coordinated simulation of the pelvic structure, the hip joint and the thigh segments with longitudinal displacement of the ground including 3-D mobility of the ground. This mechanical framework is completed by the connection of an above knee leg prosthesis equipped with at least a motorized knee joint and a motorized or a passive ankle joint in order to complete the simulation of the locomotion movements with the knee joint and the ankle joint motions. Of course other uses of the human locomotion simulator described herein are possible, such as, for example, the testing of footwear.

It is to be understood that in the foregoing the words "vertical" and "horizontal" are to be construed broadly. For example, generally orthogonal orientations would be encompassed thereby.

Mechanical Design

The human locomotion simulator 20 consists of a five degrees of freedom (DOF) system which are actively controlled by a controller or a computer network running a control software; the vertical and the horizontal linear axes of the pelvic structure, the hip-thigh mechanism (hip joint and the thigh segment) of the simulator itself, the knee joint of the motorized leg prosthesis and longitudinal displacement of the ground. Optionally, the human locomotion simulator 20 could also include the four vertical displacement pistons of the treadmill to allow for the 3-D variable positioning of the ground and a controlled ankle joint in the case where the leg prosthesis includes a active ankle joint.

Referring to FIG. 1, the mechanical components of the human locomotion simulator 20 include a base 22 onto which is mounted a conventional treadmill 24, a vertical post 26 mounted to the base 22, a pelvic structure 29 composed of a vertically movable support 28 mounted to the vertical post 26 as to produce the vertical displacement of the pelvic structure 29 and a horizontally movable support 30 so mounted to the vertically movable support 28 as to move the pelvic structure 29 horizontally, a hip-thigh mechanism 33 including a hip joint 40 represented by a pivot pin and a thigh segment assembly 38 (schematically illustrated in FIG. 1) mounted on the horizontally movable support 30 of the pelvic structure 29 providing the rotational mobility at the hip joint 40 of the thigh segment assembly 38. FIG. 1 also illustrates a schematic prosthesis leg 32 provided with a knee joint, a shank segment, a ankle joint and a foot mounted to the thigh segment assembly 38.

Figure 3:
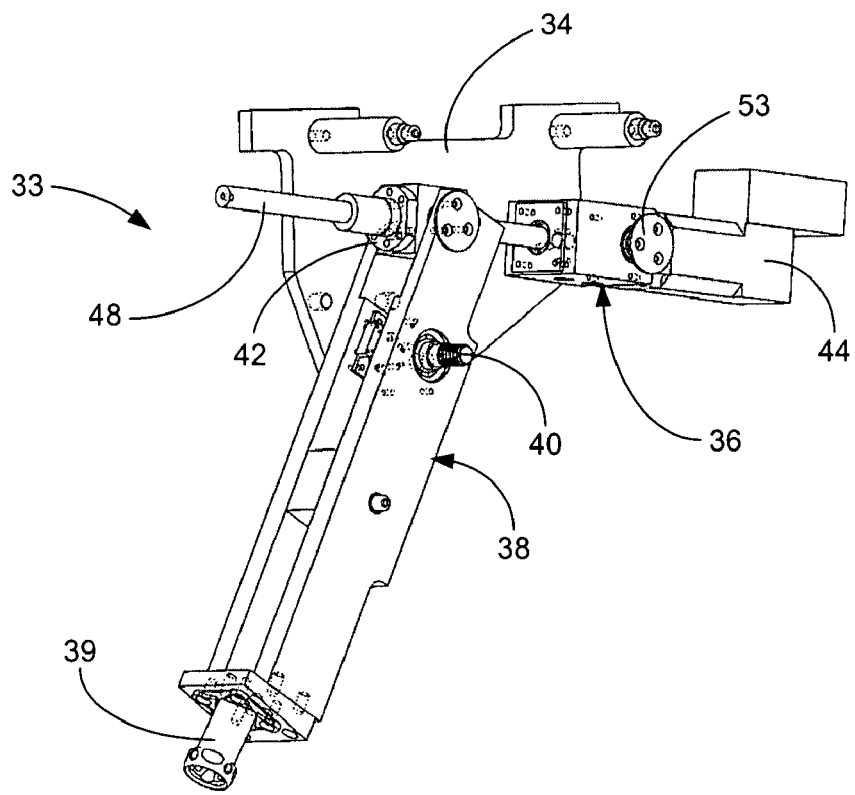
FIG. 3 is a perspective view of a hip-thigh mechanism of the human locomotion simulator of FIG. 1.

The hip-thigh mechanism 33 is illustrated in FIG. 3. It is designed to allow easy installation and maintenance of all it's components. The unit can be completely assembled before attaching to the rest of the system. And all it's sub-assemblies can be assembled or disassembled individually.

Figure 2:
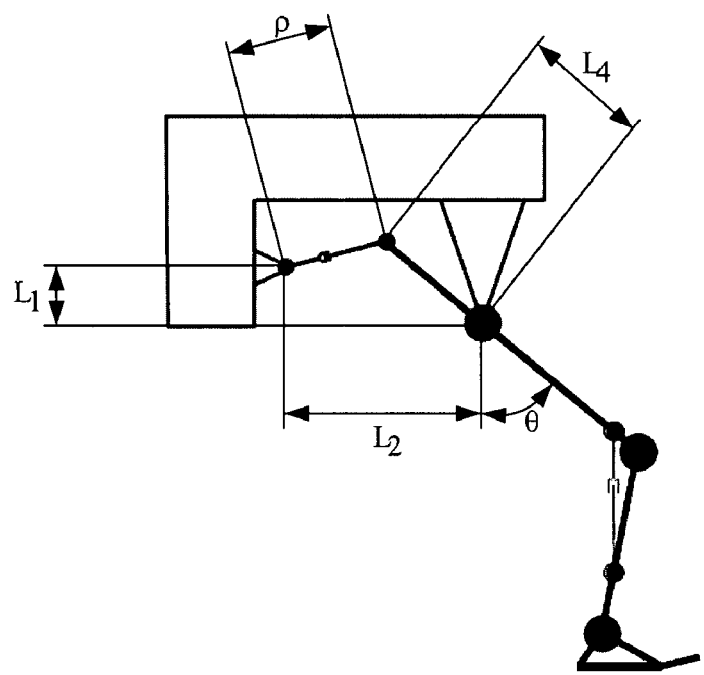
FIG. 2 is a schematic side elevational representation of a portion of the pelvic structure, the hip joint, the thigh segment, the knee joint mechanical components and the leg prosthesis similar to FIG. 1 and illustrating the various variables used in calculation.

Calculations have been done to ensure that the hip-thigh mechanism 33 can provide the required level of torque and speed with the torque and speed range of the motor. The calculation (Equation 1) is also used in the control software to translate the hip angle into linear displacement along the motor axis. The variables used in Equation 1 are shown in FIG. 2.

$$\rho = \sqrt{(L_2 + L_4 \cdot \sin\theta)^2 + (L_4 \cdot \cos\theta - L_1)^2} \quad \text{Equation 1}$$

Returning to FIG. 3, the hip-thigh mechanism 33 includes a hip frame assembly 34, a hip joint motor assembly 36 and a thigh segment assembly 38 with a connector or attachment member 39 for mounting the prosthesis leg 32.

The hip frame assembly 34 is configured and sized to be mounted to the horizontally movable support 30 of the pelvic structure 29 as will be described hereinbelow.

Figure 4:
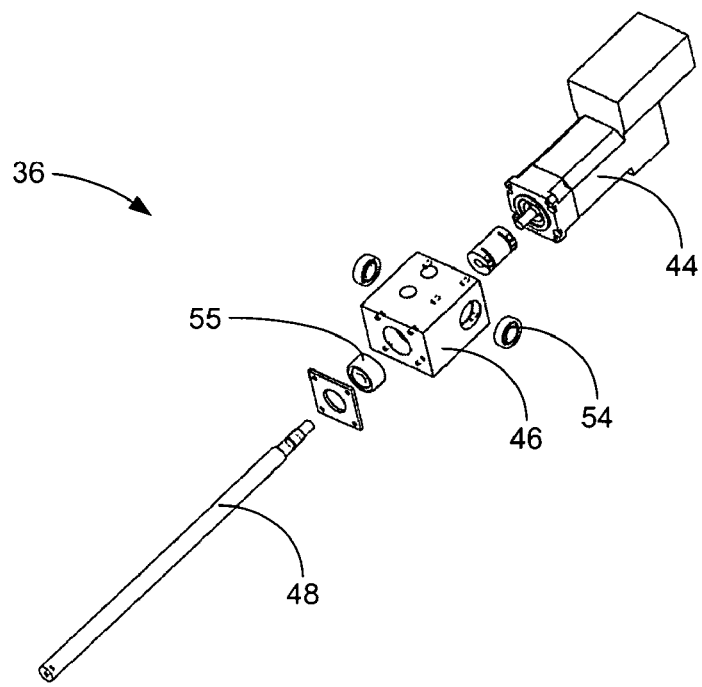
FIG. 4 is an exploded perspective view of a hip joint motor assembly of the hip-thigh mechanism of FIG. 3.

The hip joint motor assembly 36 shown in FIG. 4 is pivotally mounted to the hip frame assembly 34. The hip joint motor assembly 36 and the thigh segment assembly 38 are interconnected by a hip joint ball-nut assembly 42 shown in FIG. 5. Similarly, the thigh segment assembly 38 is pivotally mounted to the hip frame assembly 34 via a hip pivot pin 40 (FIG. 3) that simulates the biomechanical axis of the human locomotion structure at the hip.

FIG. 4 illustrates the hip joint motor assembly 36 in an exploded view. The hip joint motor assembly 36 includes a hip motor 44, a hip joint ball-screw holder 46 and a ball screw 48. The hip motor 44 is fixedly mounted to the hip joint ball-screw holder 46 that is itself pivotally mounted to the hip frame assembly 34 of FIG. 3 via bearings 54 and a fastener 52 (see FIG. 3). The ball screw 48 is mounted to the hip motor 44 to rotate therewith, passing through the angular-contact bearings set 55.

Figure 5:
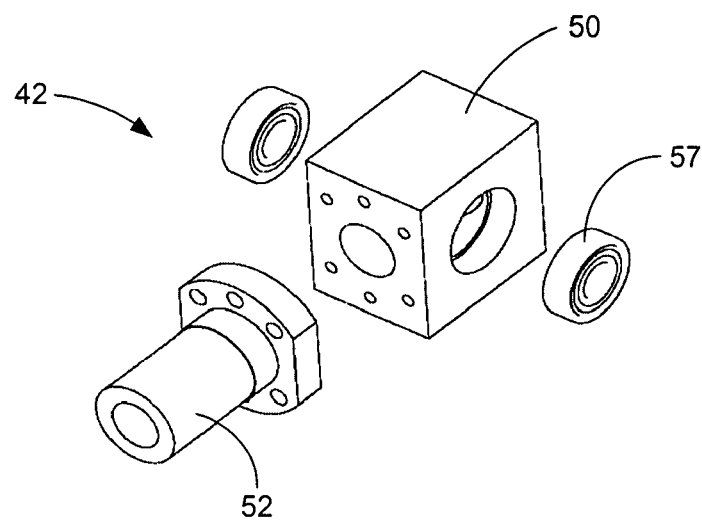
FIG. 5 is an exploded perspective view of a hip joint ball-nut assembly of the hip-thigh mechanism of FIG. 3.

The hip joint ball-nut assembly 42 is shown in an exploded view in FIG. 5. It includes a body 50 that is pivotally mounted to the thigh segment assembly 38 via bearings 57 and a threaded element 52 fixedly mounted to the body 50. The threaded element 52 is so internally threaded as to receive the externally threaded ball screw 48.

The hip joint motor assembly 36 provides a linear motion to the hip joint ball-nut assembly 42, which induces a rotational movement to thigh segment assembly 38 around the hip pivot pin 40. The ball-screw 48 is inserted into the hip joint ball screw holder 46 with angular-contact bearings set 55 in a back-to-back arrangement (see FIG. 4). Because this arrangement provides a stiff linkage between the ball screw 48 and the hip joint ball-nut assembly 42, it is necessary to have an accurate alignment between the ball screw 48 and the hip joint ball-nut assembly 42.

Figure 6:
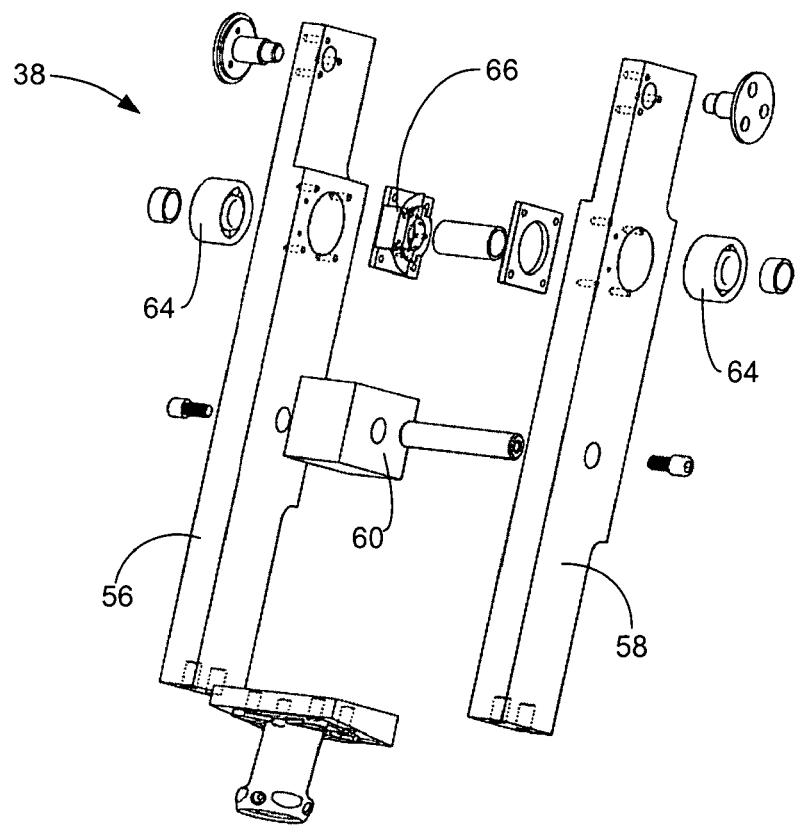
FIG. 6 is an exploded perspective view of a thigh segment assembly of the hip-thigh mechanism of FIG. 3.

The thigh segment assembly 38 is illustrated in an exploded perspective view in FIG. 6. The thigh segment assembly 38 makes the link between the prosthesis leg 32 (FIG. 1) and the horizontally movable support 30.

The thigh segment assembly 38 includes two parallel plates 56 and 58 interconnected by a spacer 60 and a bracket 62 configured and sized to mount the prosthesis leg thereto. Two toller bearings 64 are provided to pivotally mount the thigh segment assembly 38 to the hip frame assembly 34. A hip joint position sensor assembly 66 is located between the two plates 56 and 58.

Figure 7:
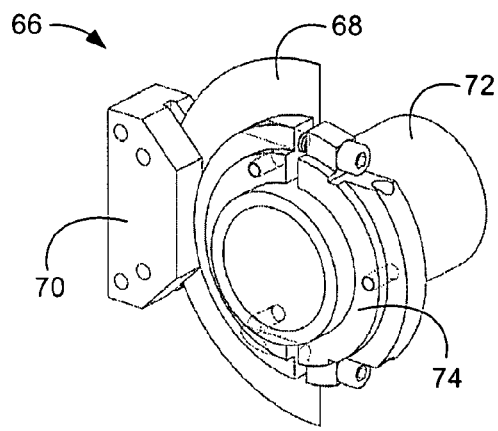
FIG. 7 is a perspective view of a hip joint position sensor assembly of the thigh segment assembly of FIG. 6.

The position measurement of the thigh segment assembly 38 is achieved via the hip joint position sensor assembly 66 illustrated in a perspective view in FIG. 7. Angular position measurement of the thigh segment assembly 38 is supplied by rotational optical sensor disk 68 installed on the hip pivot pin 40 and read by an encoder module 70. The hip joint axis sleeve 72 and hip joint sensor hub 74 receive the hip pivot pin 40 that pivotally mount the thigh segment assembly 38 to the hip frame assembly 34. Without limiting the present description, it has been found that the sensor model HEDS-9040-T00 E3-2048-1000-IHUB made by US Digital is adequate to be used as the hip position sensor assembly 66.

Turning now to FIGS. 8 to 11 of the appended drawings, the pelvic structure 29, its vertically movable support 28, its horizontally movable support 30, its attached vertical and horizontal axis movement generator assemblies and the bumper structure will be described.

Figure 9:
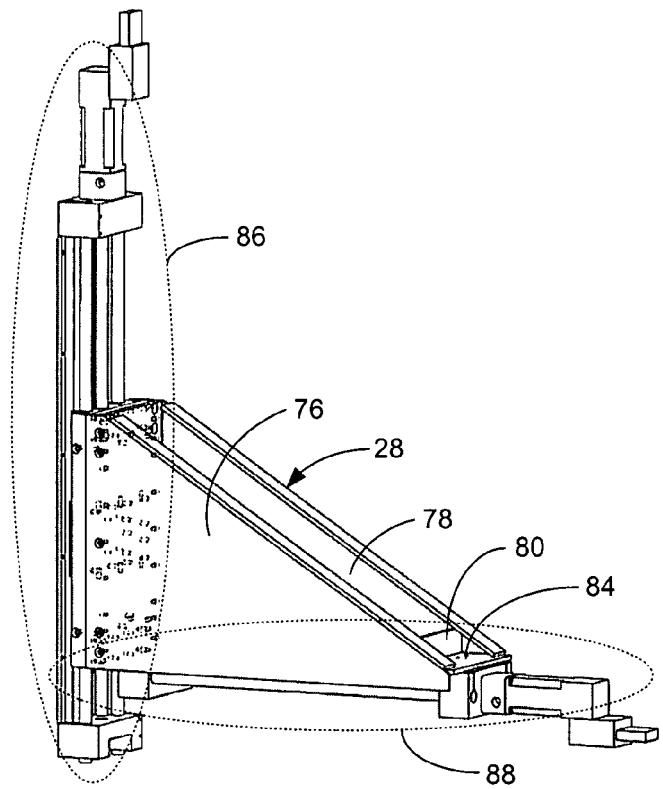
FIG. 9 is a perspective view of the vertical and horizontal axis movement generators of the pelvic structure of FIG. 8.

As can be seen from FIG. 9, the vertically movable support 28 includes a generally triangular body defined by two triangular plates 76 and 78, maintained at a predetermined spacing by spacers 80 (only one shown), and both a vertical plate 82 and a horizontal plate 84.

A vertical axis movement generator 86 is mounted to the vertical plate 82 and a horizontal axis movement generator 88 is mounted to the horizontal plate 84. The vertical and horizontal axis movement generators 86 and 88 are identical. Accordingly, for concision purposes, only the vertical axis movement generator 86 will be described hereinbelow with respect to FIG. 10.

The vertical axis movement generator 86 includes a motor 94 to which is associated a ball screw 92. A pair of linear slides 95 are mounted to the fixed portion of the motor 94. A mobile unit 96 is slidably mounted to the pair of slides 95 via linear bearings 97.

The mobile unit 96 includes a carriage portion 98 and secondary portions 100. Both portions 98 and 100 being slidably mounted to the slides 95 via the linear bearings 97.

A ball nut 102 is mounted to the carriage portion 98 of the mobile unit 96 and is engaged by the ball screw 92. Accordingly, rotation of the ball screw 92 by the motor 94 causes a linear movement of the mobile unit 96 on the slides 95.

Four springs 104 are provided between the carriage portion 98 and the secondary portions 100 of the mobile unit 96. These springs 104 are used as a suspension between the carriage portion 98 and the secondary portions 100. This suspension is interesting in the simulation of human locomotion because this type of mechanism provides the expected damping effects of the mobility of the vertical movable support 28 of the pelvic structure 29, as will easily be understood by one skilled in the art. The four springs 104 are part of the Series Elastic Actuators (SEA) that are used to control the force applied on the corresponding vertical and horizontal movable supports 28 or 30. These springs 104 allow the simulation of various persons weight and to separate the inertia of the actuator from the inertia of the vertical and horizontal movable supports 28 and 30.

In other words, the linear slides 95 and linear bearings 97 guide the movement and the actuation is provided by a combination of motor 94, ball-screw 92 and ball-nut 102. The vertical and horizontal axis movement generators 86 and 88 are controlled in position and force and use a special mechanism and sensors to perform this task as will be described hereinbelow.

The position control loop utilizes position sensors 99 to get position feedback on both vertical and horizontal axes. Without limiting the present disclosure, Table 1 presents the technical information on linear optical sensors that have been found suitable to be used as position sensors 99.

TABLE 1

Horizontal and vertical position feedback sensors

| Axis | Position Feedback Sensor | | |
|---|---|---|---|
| | Type | Model | Resolution |
| Vertical | Linear optic | US Digital EMI-0-250 LIN-250-16-S2037 | 1/250 inch (0.1 mm) |
| Horizontal | Linear optic | US Digital EMI-0-250 LIN-250-16-S2037 | 1/250 inch (0.1 mm) |

Force sensors are used to measure the force levels applied on the vertical and horizontal axes. Those sensors measure the displacement between the carriage portion 98 and the secondary portions 100 of the mobile unit 96 for each axe. The secondary portions 100 being linked to the carriage portion 98 with springs 104, the applied force is a function of the displacement between the two portions (98, 100) and of the known strength of the springs 104. Force sensors advantageously require fine position measurement accuracy. Therefore, magnetic stripe technology was selected. Without limiting the present disclosure, Table 2 presents the technical information on linear magnetic sensors that have been found adequate for this application. Along with the linear magnetic sensors, an index sensor is used to determine the reference position.

TABLE 2

Horizontal and vertical force feedback sensors

| Axis | Force Feedback Sensor | | |
|---|---|---|---|
| | Type | Model | Resolution |
| Vertical | Linear magnetic | SIKO MSK200/1 MB200 | 4 µm |
| Horizontal | Linear magnetic | SIKO MSK200/1 MB200 | 4 µm |

Figure 11:
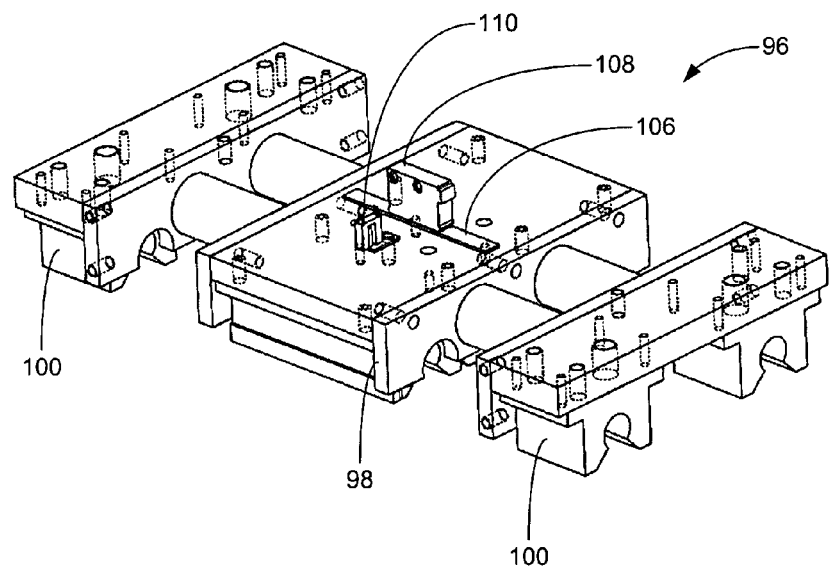
FIG. 11 is a perspective view of a portion of the vertical axis movement generator illustrating the mounting of the force sensors.
Figure 12:
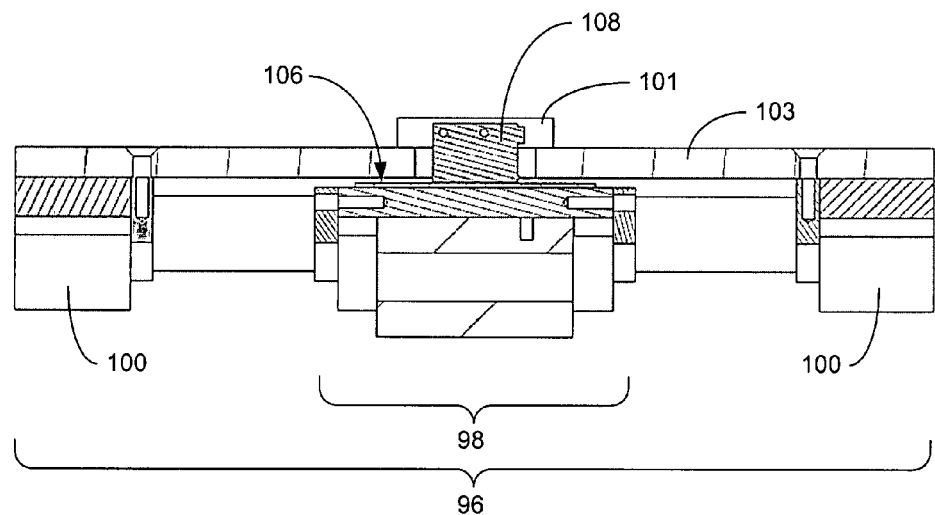
FIG. 12 is a sectional side elevation view of the vertical axis movement generator of FIG. 10, illustrating the magnetic sensor thereof.
Figure 13:
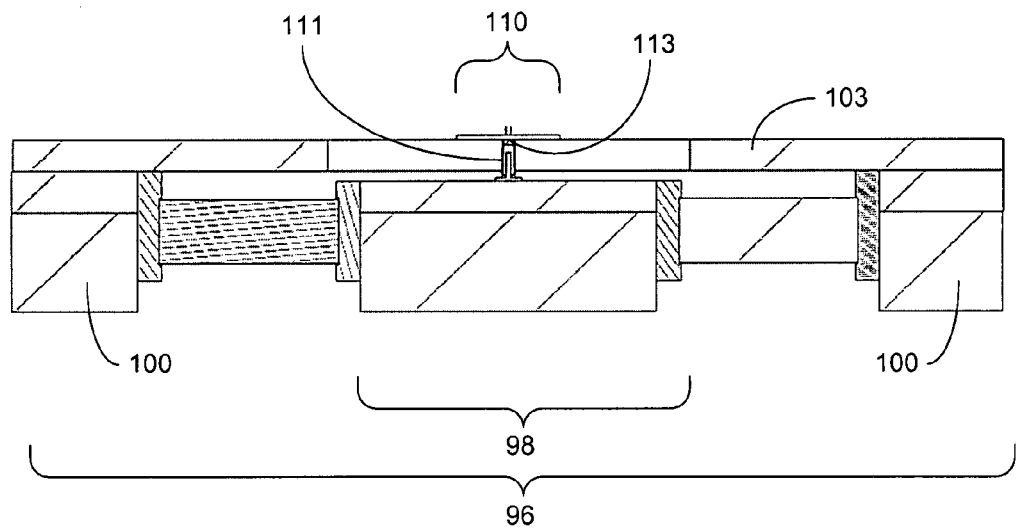
FIG. 13 is a sectional side elevation view of the vertical axis movement generator of FIG. 10, illustrating the photo sensor thereof.

Turning now to FIGS. 11 to 13, the linear magnetic sensors will be described. FIG. 11 illustrates, in a perspective view, the mobile unit 96 of the vertical axis movement generator 86 without the slides 95 and the motor 94. A magnetic stripe 106 is attached to the carriage portion 98 and a linear magnetic sensor 108 is in close proximity to the magnetic stripe 106 and is designed to be rigidly connected to the secondary portions 100. More specifically, as can be better seen from FIG. 12, the linear magnetic sensor 108 is secured to a bracket 101 itself mounted to a plate 103 that connects to the secondary portions 100. Therefore, relative displacement of the carriage portion 98 with respect to the secondary portions 100 is detected and measured by the linear magnetic sensor 108.

An optical index sensor 110 is also mounted to the carriage portion 98. The optical index sensor 110 serves as a means to determine the absolute home position of the linear magnetic sensor 108. As can be better seen from FIG. 13, the index sensor 110 includes a thin opaque mask 111 attached to the carriage 98 that moves between the emitter and the receptor of a photo sensor 113 attached to the plate 103 of the mobile unit 96. For example, and without limiting the present disclosure, it has been found that a transmissive photomicrosensor made by Omron under model number EE-SX1042 has been found suitable for the present application.

The actuators used to move the mobile units of the vertical and horizontal axis movement generator 86 and 88 are Series Elastics Actuators (SEA). These actuators are mechanisms that allow to control position and force while eliminating undesired inertia of the drive system. Since SEA actuators are believed well known in the art they will only be briefly discussed herein.

Figure 10:
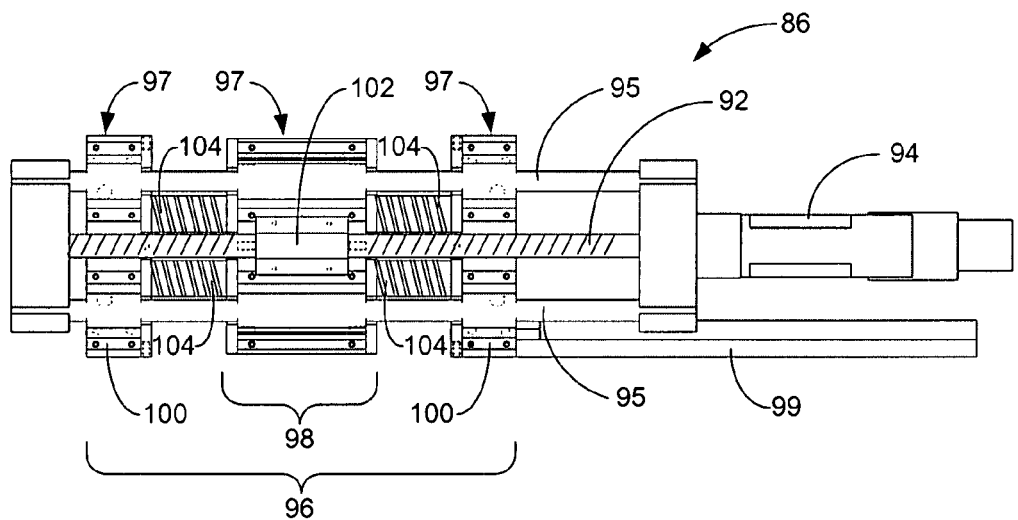
FIG. 10 is a top plan view of the vertical axis movement generator of the pelvic structure of FIG. 8.

Referring to FIG. 10, the present implementation of the SEA consists of a motor 94 and a motor drive transmission (ball-screw 92 and ball-nut 102) connected at the output of the motor 94. An elastic element, in the form of the four springs 104, is connected in series with the motor drive transmission, and this elastic element is positioned to alone support the full weight of any load connected at an output of the actuator. Referring to FIG. 11, a position sensor, in the form of the linear magnetic sensor 108 positioned between the carriage 98 and the mobile unit 96 generates a signal proportional to the deflection of the elastic element and indicates the force applied by the elastic element to the output of the actuator.

Figure 8:
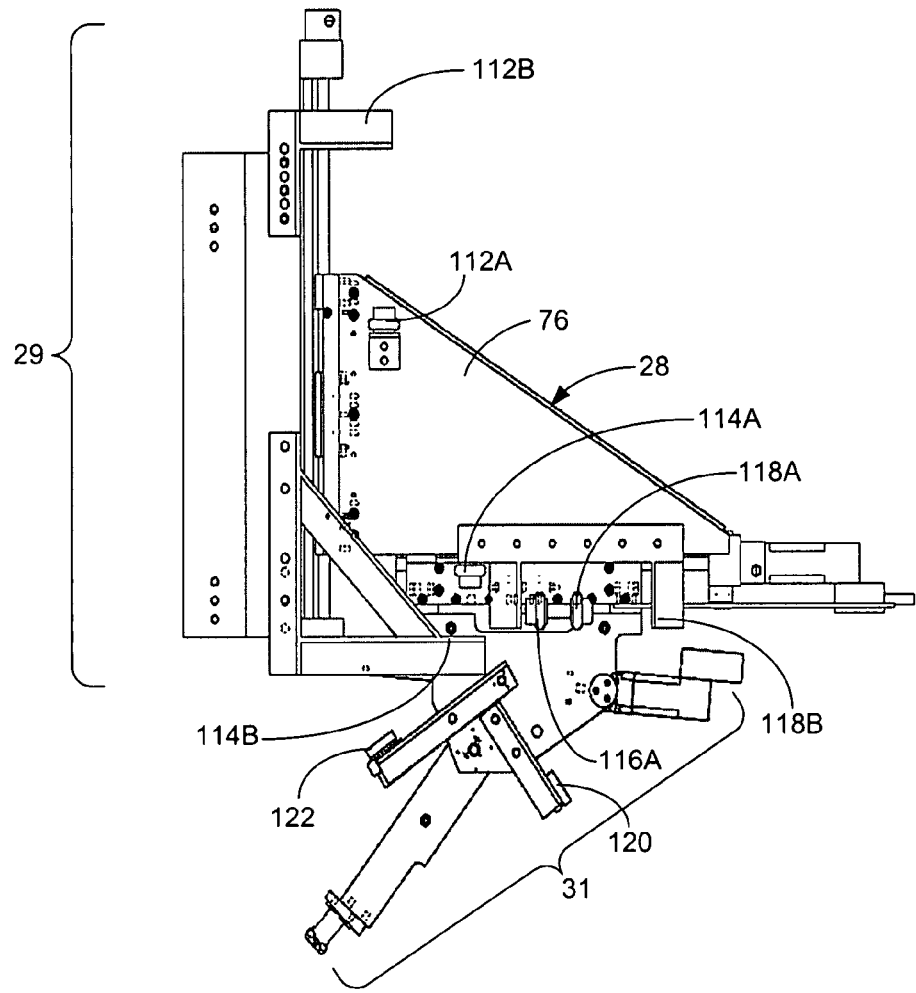
FIG. 8 is a side elevational view of a pelvic structure and the hip-thigh mechanism portion of the human locomotion simulator of FIG. 1, illustrating the various bumper structures of the simulator.
Figure 14:
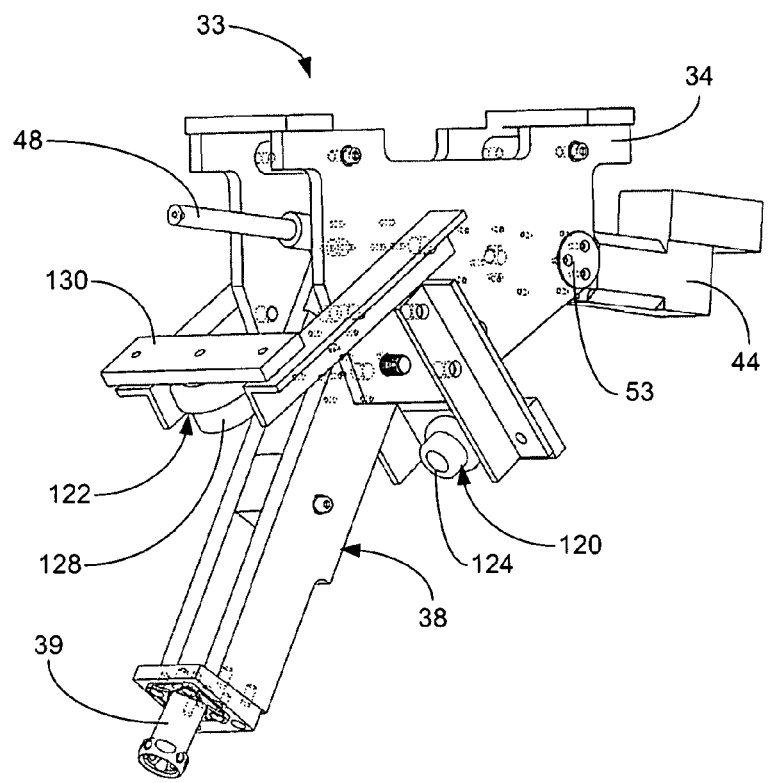
FIG. 14 is a perspective view of the hip-thigh mechanism of the human locomotion simulator of FIG. 1, illustrating the thigh bumpers.

Referring now to FIGS. 8 and 14 of the appended drawings, the bumper structure will be described. The bumper structure is so designed that each axis is completely independent. The bumper structure includes an upper vertical bumper assembly 112, a lower vertical bumper assembly 114, a front horizontal bumper assembly 116, a back horizontal bumper assembly 118, a back thigh bumper bracket 120 and a front thigh bumper bracket 122.

It is to be noted that even though only one of each bumper assembly 112, 114, 116 and 118 is illustrated in FIG. 8, two of each of these assemblies are present, one for each side of the simulator.

The upper vertical bumper assembly 112 includes a bumper 112A mounted to the triangle plate 76 of the vertically movable support 28 and a stop bracket 112B, mounted to the vertical post 26 (see FIG. 1) and vertically aligned with the bumper 112A to upwardly stop the course of the vertically movable support 28. Similarly, the lower vertical bumper assembly 114 includes a bumper 114A mounted to the triangle plate 76 of the vertically movable support 28 and a stop bracket 114B, mounted to the vertical post 26 and vertically aligned with the bumper 114A to stop the course of the vertically movable support 28 at the lowers desired position.

The front horizontal bumper assembly 116 includes a bumper 116A and the back horizontal bumper assembly 118 includes a bumper 118A where the both bumper 116A and 118A are positioned on the mobile unit of the horizontal axis movement generator 88. The front and back horizontal bumpers assembly 116, 118 share a common stop bracket screwed on the triangle plate 76 of the vertically movable support 28 providing the front stop bracket 116B and the stop bracket 118B. Front and rear movement of the hip-thigh mechanism 33 is stopped by the contact of the bumpers 116A, 118A with the stop bracket portions 116B and 118B, respectively.

Referring to FIG. 14, the back thigh bumper bracket 120 includes a bumper 124 and a bracket 126 positioned to the hip frame assembly 34. Similarly, front thigh bumper bracket 122 includes a bumper 128 and a bracket 130 positioned to the hip frame assembly 34. The thigh bumper brackets 120 and 122 limit the movement of the thigh segment assembly 38.

The bumpers were selected such that the system's kinetic energy can be absorbed by the bumpers. All bumpers are the same, simply for standardization. The worst case condition that produces the highest kinetic energy level is when the system stands at the highest point and is let down in free-fall. The motor of the vertical axis movement generator 86 could also add to the total energy, but its contribution is negligible compared to the free-fall. Both bumper 114A of the lower vertical bumper assembly 114B and the bumper 128 of the front thigh bumper bracket 122 shall be able to sustain the free-fall drop. The condition where the bumper 128 can be solicited is when the foot enters in contact with the floor before the said bumper 114A hits its respective stop bracket 114B. The total energy is calculated as follow:

$E = F * d;$ $F = 9.8 \text{ m/s}^2 * 70 \text{ kg} = 686 \text{ N};$ $d = 0.28 \text{ m; and}$ $E = 686 \text{ N} * 0.28 \text{ m} = 192 \text{ N.m} = 1700 \text{ lb.in.}$ Therefore, each bumper should be able to sustain about 1700 lb.in. Miner's GBA-5 bumpers or one GBA-9 meet this requirement. One skilled in the art will understand that the range of motion of the vertically movable support 28 can be adjusted by changing the position of respective stop brackets 112B, 114B, 116B, 118B, 120 and 122 or their corresponding bumpers 112A, 114A, 116A and 118A.

From the kinetics standpoint, all joints provide enough force/torque to simulate the locomotion activities characterizing a human subject, which mass is corresponding to the mechanical simulator lower-limb linkage (i.e., about 72.5 kg in the illustrated embodiment) by adequately mobilizing the vertically and horizontally movable supports 28 and 30 of the pelvic structure 29, the hip-thigh mechanism 33 and the thigh segment assembly 38.

Another aspect of the present invention is concerned with the simulation of human locomotion in stairs. In order to simplify the simulation approach, limit the number of subsystems required, minimize modifications to the actual platform design, and facilitate integration with the actual level-walking simulation capabilities of the platform, the implementation of a complete stance phase simulation with a modified swing phase using the treadmill was proposed over the use of an approach requiring the use of a stepmill-like device. In the proposed approach, the treadmill moving surface is used to simulate the step tread as well as the velocity corresponding to the horizontal progression speed of a normal human subject climbing or descending stairs.

This approach allows to correctly simulate the pelvic, the hip and the knee joint mobility during both stairs ascent and descent tasks stance phase, while the swing phase needs to be modified to account for the limited motion range available on the platform and in order to generate coherent stance initial conditions. The swing phase trajectories modifications mostly affect the vertical and horizontal degrees-of-freedom and do not harm the overall simulation validity in a significant manner of this type of locomotion and more specifically the respective stance phase.

Figure 15:
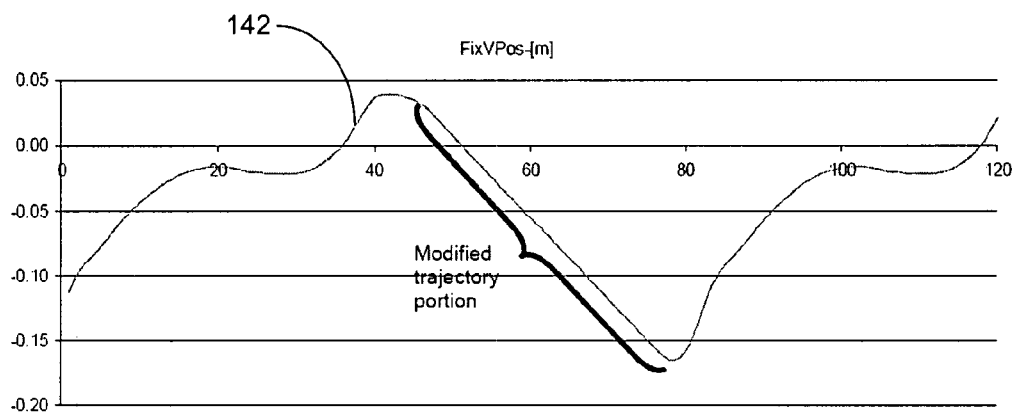
FIG. 15 is a graph showing the displacement as a factor of time in an example of a modified trajectory.
Figure 16:
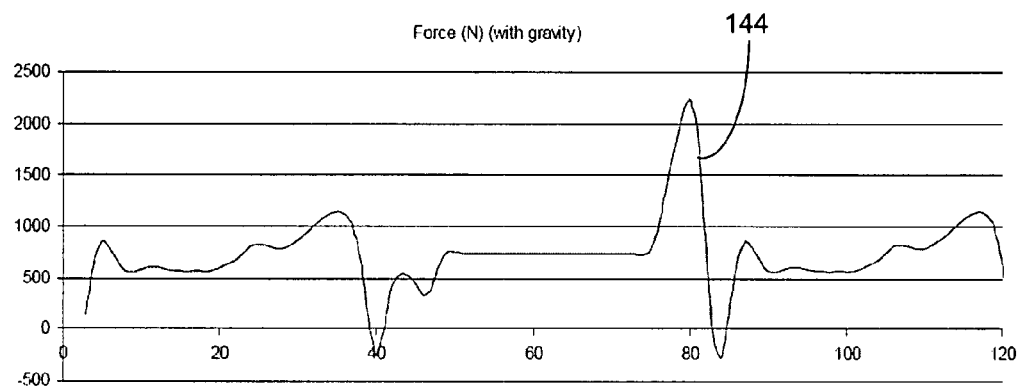
FIG. 16 is a graph showing the exerted vertical force as a factor of time in an example of a modified trajectory.
Figure 3:
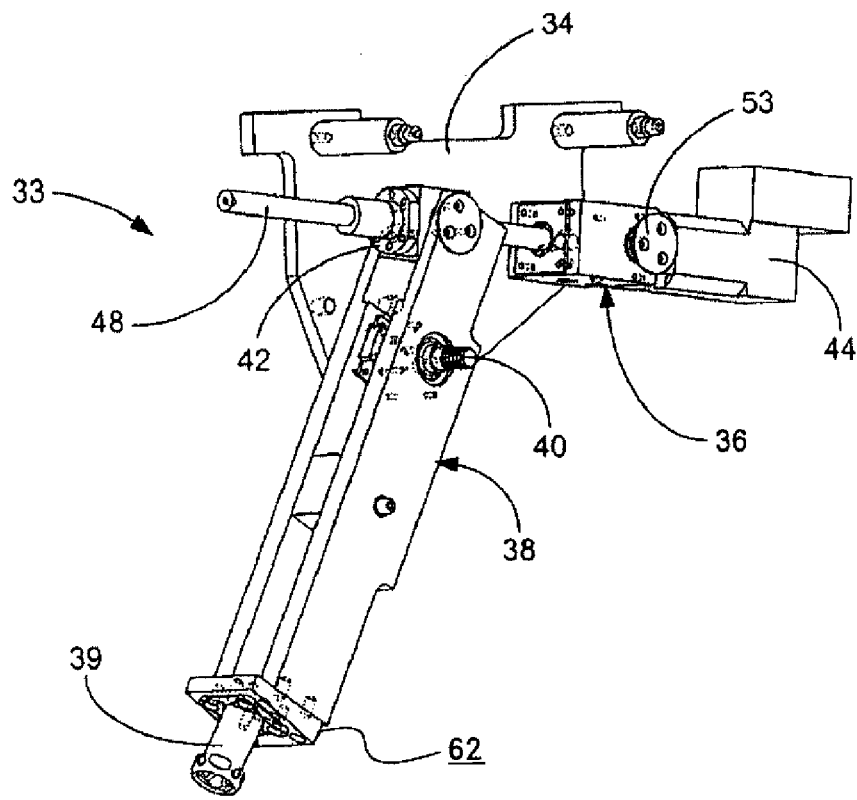
Figure 4:
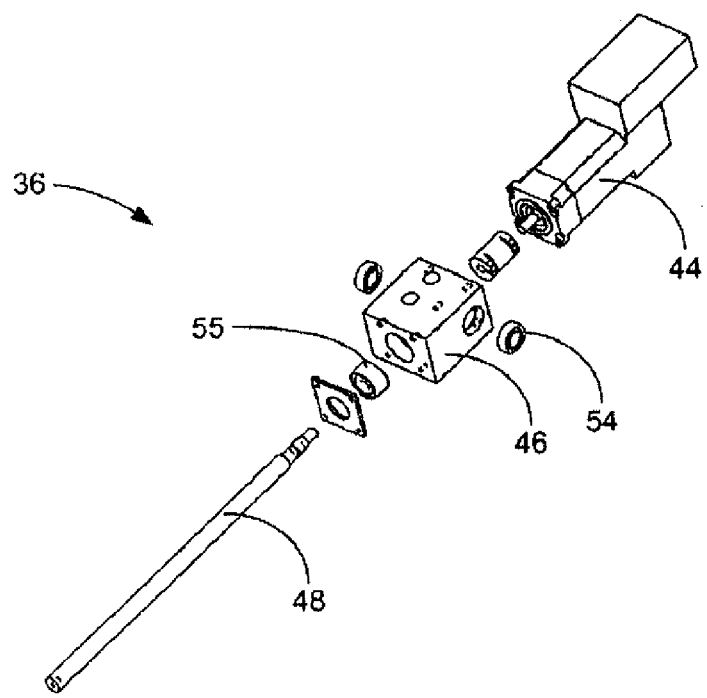
Figure 5:
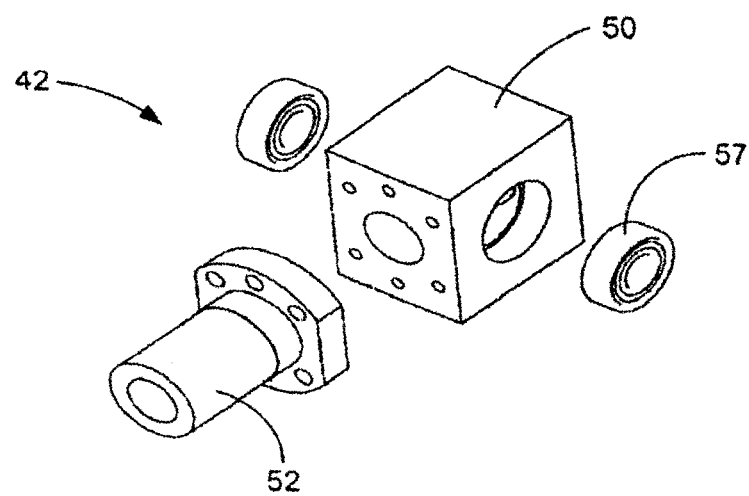
Figure 6:
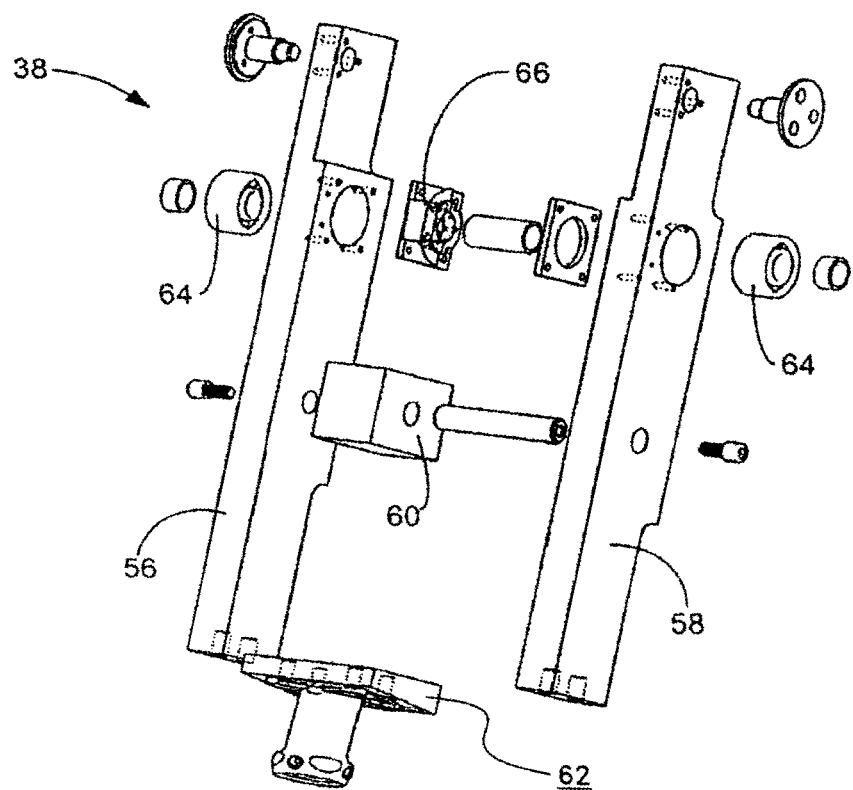
Figure 7:
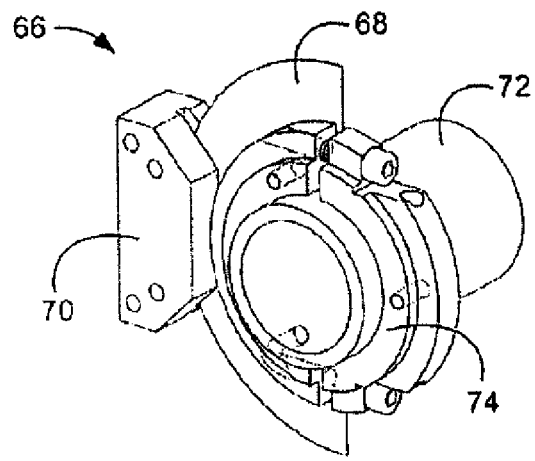
Figure 8:
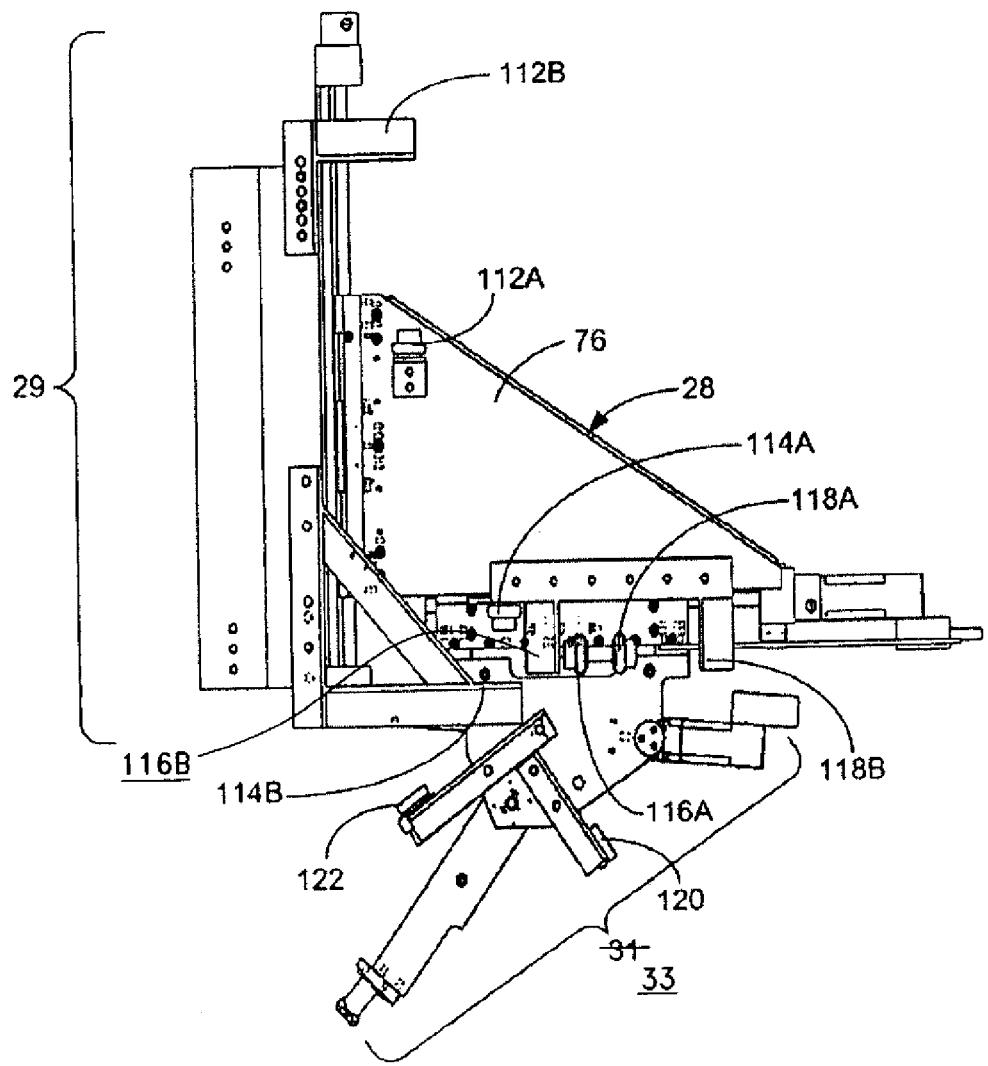
Figure 9:
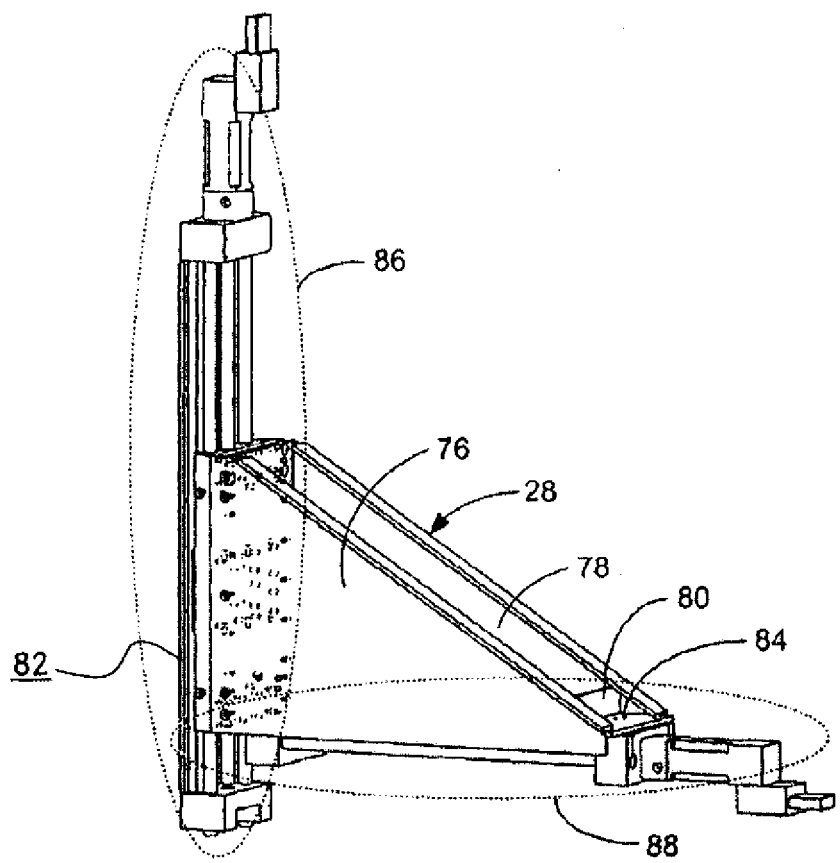
Figure 10:
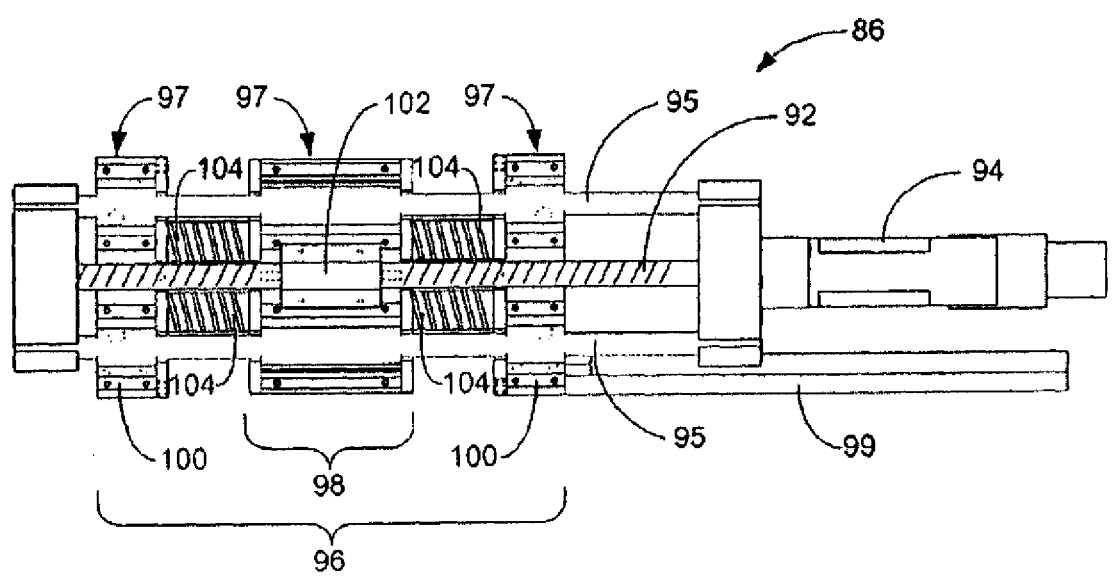
Figure 13:
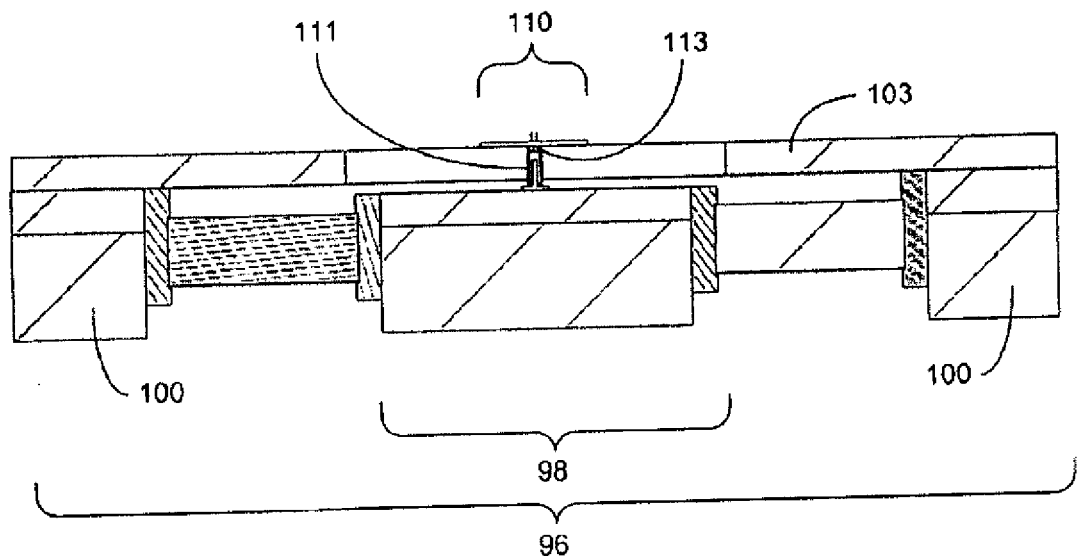
Figure 14:
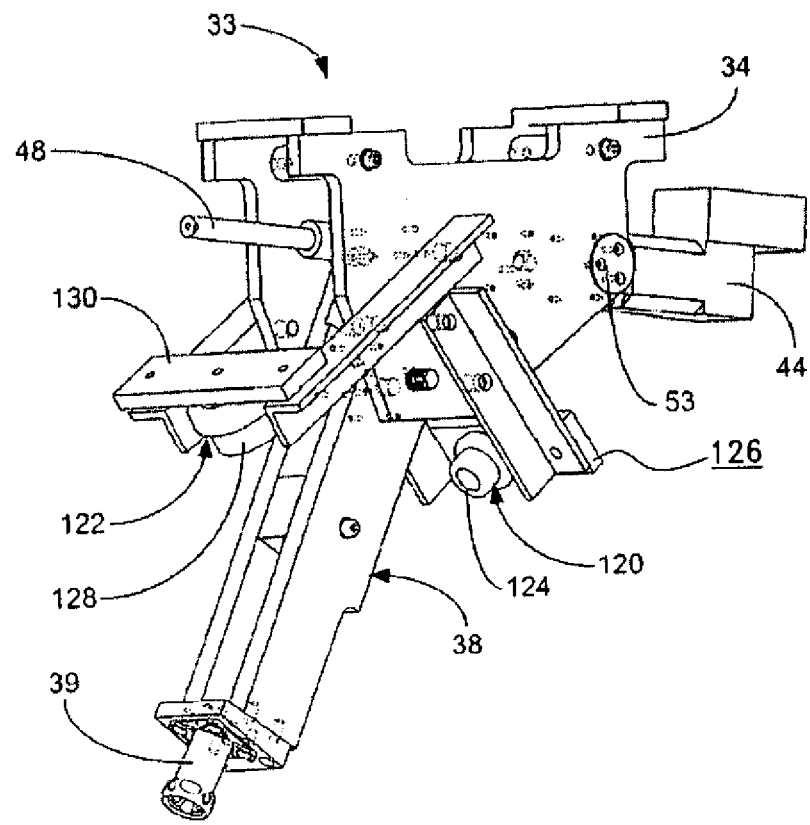

The range of motion provided by the vertical, horizontal displacement of the pelvic structure 29 and the rotational displacement of the thigh segment assembly 38, combined with the constant treadmill 24 movement, allows the simulation of the desired tasks: level walking, ascending and descending stairs. The trajectory of the vertical axis of the pelvic structure 29 has been modified (as can be seen in FIGS. 15 and 16) for the stair ascent and descent to address the fact that the simulator's 20 flat treadmill 24 approach doesn't allow natural kinematics during those tasks. For example, at the end of the stance phase of a step during stair ascent, the pelvic structure 29 would normally continue going up until the next step, but due to the limited vertical freedom of movement on the simulator 20, the body of the simulator 20 will go down during the swing phase and ensure that the foot is placed properly on the treadmill 24 for the next step.

FIGS. 15 and 16 show an example of how the vertical axis motion of the pelvic structure 29 is modified for the stairs ascent. The graph of FIG. 15 displays the modified displacement 142 during the stair ascent simulation whereas the FIG. 16 displays the force level 144 required on the vertical axis to follow the desired trajectory. The trajectory displacement 142 and the exerted vertical force 144 represent the kinematics and the kinetics respectively of the vertical mobility of the pelvic bone of the human body.

It is to be noted that the forces displayed in FIG. 16 represent the vertical forces to be applied in order to precisely follow the given trajectory, with the assumption that there is no ground contact. This assumption provides force levels that are at least as high as with ground contact condition. It is obvious that the highest force peaks originate from the modification of the trajectory instead of the original gait motion itself (high acceleration level at the end of the modified trajectory).

All three axes of the simulator 20 are driven by drive systems that allow following their respective trajectories while providing the required level of forces and accelerations. The range of motion was established directly from the trajectory to follow, and the required motor forces are computed from acceleration levels to reach and from the masses/inertias of the moving bodies. To select the different components of a drive system (electric drive/motor/screw), the motor torques and speeds are computed and compared with the capacity chart of the drive system.

Dimensions and Specifications of a Simulator

Without limiting the present disclosure, we present here below an example of dimensions and specifications that could be used to build the simulator 20.

Referring to FIG. 2, the following dimensions have been used:

$L_1$=80.0 mm;
$L_2$=210.0 mm;
$L_4$=103.08 mm

The distance between the hip joint 40 and the prosthesis knee axis was selected as 403.34 mm.

Without limiting the present inventions, Table 3 specifies the axes characteristics:

TABLE 3

Axes characteristics

| Axis | Range | Motor type | BUS | Screw lead | Force/Torque |
|---|---|---|---|---|---|
| Vertical: | 300 mm | Baldor | 160 | 20 mm | −5691 N |
| Horizontal: | 105 mm | Baldor BSM50N-333 | 160 VDC | 20 mm | −1709 N +1709 N |
| Hip: | −60° +30° | Baldor BSM50N-333 | 160 VDC | 10 mm | −228 Nm +228 Nm |
| Treadmill: | 0.8 km/h 16 km/h | Drive and control from Schwinn | N/A | N/A | N/A |

Table 4 indicates the characteristics of the position and force feedback sensors:

TABLE 3

Position and force feedback sensors characteristics

| | Force Feedback Sensor | | | Position Feedback Sensor | | |
|---|---|---|---|---|---|---|
| Axis | Type | Model | Resolution | Type | Model | Resolution |
| Vertical | Linear magnetic | SIKO MSK200/1 MB200 | 4 μm | Linear optic | US Digital EMI-0-250 LIN-250-16-S2037 | 1/250 inch (0.1 mm) |
| Horizontal | Linear magnetic | SIKO MSK200/1 MB200 | 4 μm | Linear optic | US Digital EMI-0-250 LIN-250-16-S2037 | 1/250 inch (0.1 mm) |
| Hip | N/A | N/A | N/A | Rotational optic | US Digital HEDS-9040-T00 E3-2048-1000-IHUB | 1/2048 turn (0.18°) |

The vertical and horizontal axes of the pelvic structure 29 are controlled in position and force (see FIG. 11). Position control is conventional, and relatively straightforward. Force control is utilized to eliminate the appearance of inertia induced by the drive system. In the case of the vertical axis of the pelvic structure 29, the mass of the system is about 75 kg, but for the reason that the motor/ball screw system rotates when the mass moves vertically, the apparent mass when accelerations are induced would increase to about 85 kg (apparent inertia). The force control mechanism allows eliminating the additional apparent inertia of the drive system. This system also allows simulating weights different than the system's weight by requesting the desired level of force on the force control loop.

Although the present invention has been described by way of particular embodiments and examples thereof, it should be noted that it will be apparent to persons skilled in the art that modifications may be applied to the present particular embodiment without departing from the scope of the present invention.

What is claimed is:

1. A locomotion simulator comprising:
a base having a surface movable along a base axis;
a post mounted to the base;
a pelvic structure including:
a first support movably mounted to the post, the first support allowing a displacement of the pelvic structure along a first pelvic axis generally perpendicular to the base axis;

a second support movably mounted to the first support, the second support allowing a displacement of the pelvic structure along a second pelvic axis generally parallel to the base axis;

a hip-thigh mechanism mounted to the second support, the hip-thigh mechanism including:

a hip joint having a pivot axis generally perpendicular to the displacement of the second support;

a thigh segment assembly pivotally so connected to the hip joint as to pivot in a plan defined by the first and second pelvic axes;

wherein coordinated displacement of the pelvic structure and pivoting of the thigh segment assembly simulates patterns of locomotion.

2. A locomotion simulator according to claim 1, wherein the movable surface includes a treadmill.

3. A locomotion simulator according to claim 1, further comprising a controller for coordinating the displacement of the pelvic structure and the pivoting of the thigh segment assembly.

4. A locomotion simulator according to claim 1, wherein the range of pivotal movement of the thigh segment assembly is limited by a bumper assembly.

5. A locomotion simulator according to claim 1, wherein the movable surface can further be oriented so that the base axis defines an angle with the second pelvic axis.

6. A locomotion simulator according to claim 5, further comprising four displacement pistons provided between the base and the movable surface to allow the orientation of the movable surface with respect to the base.

7. A locomotion simulator according to claim 1, further comprising an above-knee prosthesis mounted to the thigh segment assembly, the prosthesis having a motorized knee joint, an ankle joint and a foot.

8. A locomotion simulator according to claim 7, wherein the ankle joint is motorized.

9. A locomotion simulator according to claim 1, wherein the hip-thigh mechanism further includes a hip frame assembly mounted to the second support and a hip joint motor assembly pivotally mounted to the hip frame assembly, the hip joint motor assembly being connected to the thigh segment assembly and the thigh segment assembly being pivotally mounted to the hip frame assembly via the hip joint.

10. A locomotion simulator according to claim 9, further comprising a hip position sensor.

11. A locomotion simulator according to claim 10, wherein the hip position sensor if located on the hip joint.

12. A locomotion simulator according to claim 11, wherein the hip position sensor includes a rotational optical sensor disk and an encoder module.

13. A locomotion simulator according to claim 1, wherein the displacement of the pelvic structure in the first pelvic axis is produced by a first movement generator interconnecting the post and the first support.

14. A locomotion simulator according to claim 13, wherein the first movement generator includes a first serial elastic actuator.

15. A locomotion simulator according to claim 14, wherein the first serial elastic actuator includes: a fixed portion mounted to the post and provided with parallel slides defining the first pelvic axis, a motor provided with a ball screw and a mobile unit so mounted to the parallel slides as to be movable along the first pelvic axis.

16. A locomotion simulator according to claim 15, wherein the mobile unit is mounted to the fixed portion via linear bearings.

17. A locomotion simulator according to claim 15, wherein the mobile unit is interconnected to the ball screw via a ball nut allowing rotational movements of the ball screw generated by the motor to be transformed into linear movements of the mobile unit along the first pelvic axis.

18. A locomotion simulator according to claim 15, further including a bumper assembly to limit the movement of the mobile unit with respect to the fixed portion.

19. A locomotion simulator according to claim 15, wherein the mobile unit includes first and second secondary portions mounted to both parallel slides via linear bearings, a carriage provided between the first and second secondary portions and mounted to both parallel slides via linear bearings and first and second dampeners respectively provided between the first and second secondary portions and the carriage; the carriage being mounted to the second support.

20. A locomotion simulator according to claim 19, wherein the first and second dampeners include springs.

21. A locomotion simulator according to claim 1, wherein the displacement of the pelvic structure in the second pelvic axis is produced by a second movement generator interconnecting the first support and the second support.

22. A locomotion simulator according to claim 21, wherein the second movement generator includes a second serial elastic actuator.

23. A locomotion simulator according to claim 22, wherein the second serial elastic actuator includes: a fixed portion mounted to the first support and provided with parallel slides defining the second pelvic axis, a motor provided with a ball screw and a mobile unit so mounted to the parallel slides as to be movable along the second pelvic axis.

24. A locomotion simulator according to claim 23, wherein the mobile unit is mounted to the fixed portion via linear bearings.

25. A locomotion simulator according to claim 23, wherein the mobile unit is interconnected to the ball screw via a ball nut allowing rotational movements of the ball screw generated by the motor to be transformed into linear movements of the mobile unit along the second pelvic axis.

26. A locomotion simulator according to claim 23, further including a bumper assembly to limit the movement of the mobile unit with respect to the fixed portion.

27. A locomotion simulator according to claim 23, wherein the mobile unit includes first and second secondary portions mounted to both parallel slides via linear bearings, a carriage provided between the first and second secondary portions and mounted to both parallel slides via linear bearings and first and second dampeners respectively provided between the first and second secondary portions and the carriage; the carriage being mounted to the hip-thigh mechanism.

28. A locomotion simulator according to claim 27, wherein the first and second dampeners include springs.

29. A locomotion simulator according to claim 1, wherein the first support includes a first position sensor.

30. A locomotion simulator according to claim 29, wherein the first position sensor includes a linear optical sensor.

31. A locomotion simulator according to claim 1, wherein the first support includes a first force sensor.

32. A locomotion simulator according to claim 31, wherein the first force sensors includes a linear magnetic sensor combined with an index sensor.

33. A locomotion simulator according to claim 1, wherein the second support includes a second position sensor.

34. A locomotion simulator according to claim 33, wherein the second position sensor includes a linear optical sensor.

35. A locomotion simulator according to claim 1, wherein the second support includes a second force sensor.

36. A locomotion simulator according to claim 35, wherein the second force sensors includes a linear magnetic sensor combined with an index sensor.

* * * * *

UNITED STATES PATENT AND TRADEMARK OFFICE
CERTIFICATE OF CORRECTION

PATENT NO. : 7,597,017 B2  
APPLICATION NO. : 11/880164  
DATED : October 6, 2009  
INVENTOR(S) : Stephane Bedard et al.

Page 1 of 6

It is certified that error appears in the above-identified patent and that said Letters Patent is hereby corrected as shown below:

On the Title Page, At (57) ABSTRACT, please change "plan" to --plane--.

In the Drawings

Delete Drawing Sheets 2-5 and 7 and substitute therefore the attached Drawing Sheets 2-5 and 7.

In the Specifications

At Column 4, Line 34, please change "52" to --53--.
At Column 11, Line 10, please change "plan" to --plane--.
At Column 11, Line 46, please change "if" to --is--.

Signed and Sealed this
Eighth Day of April, 2014

Michelle K. Lee
*Deputy Director of the United States Patent and Trademark Office*